(12) United States Patent
Al-Daous

(10) Patent No.: US 12,383,889 B2
(45) Date of Patent: Aug. 12, 2025

(54) IRON-DOPED POTASSIUM-TITANATE NANOTUBE CATALYSTS AND METHODS OF MAKING AND USING SAME

(71) Applicant: Saudi Arabian Oil Company, Dhahran (SA)

(72) Inventor: Mohammed Abdulmajeed Al-Daous, Jeddah (SA)

(73) Assignee: Saudi Arabian Oil Company, Dhahran (SA)

( * ) Notice: Subject to any disclaimer, the term of this patent is extended or adjusted under 35 U.S.C. 154(b) by 65 days.

(21) Appl. No.: 18/106,182

(22) Filed: Feb. 6, 2023

(65) Prior Publication Data

US 2024/0261766 A1 Aug. 8, 2024

(51) Int. Cl.
| | | |
|---|---|---|
| *B01J 23/78* | (2006.01) | |
| *B01J 35/23* | (2024.01) | |
| *B01J 35/30* | (2024.01) | |
| *B01J 35/61* | (2024.01) | |
| *B01J 35/63* | (2024.01) | |
| *B01J 37/00* | (2006.01) | |
| *B01J 37/03* | (2006.01) | |
| *B01J 37/04* | (2006.01) | |
| *C07C 1/12* | (2006.01) | |

(52) U.S. Cl.
CPC .............. *B01J 23/78* (2013.01); *B01J 35/23* (2024.01); *B01J 35/393* (2024.01); *B01J 35/394* (2024.01); *B01J 35/615* (2024.01); *B01J 35/633* (2024.01); *B01J 37/009* (2013.01); *B01J 37/031* (2013.01); *B01J 37/04* (2013.01); *C07C 1/12* (2013.01); *C07C 2523/78* (2013.01)

(58) Field of Classification Search
CPC . B01J 23/78; B01J 35/23; B01J 35/393; B01J 35/394; B01J 35/615; B01J 35/633; C10G 2/32
See application file for complete search history.

(56) References Cited

U.S. PATENT DOCUMENTS

| | | |
|---|---|---|
| 8,658,126 B2 | 2/2014 | Toledo Antonio et al. |
| 2008/0160311 A1* | 7/2008 | Tani ...................... B82Y 40/00 428/407 |

FOREIGN PATENT DOCUMENTS

| | | |
|---|---|---|
| EP | 2848589 | 3/2015 |
| EP | 2883839 | 9/2018 |

OTHER PUBLICATIONS

Sinel at al (glass physis and chemistry (2018), 44(4), 329-332).*
Roy et al., titanium nanotube synthesis, (Angew. Chem. Int. Ed. 2011, 50, 2904-2939).*
Boreriboon et al., "Fe-Based Bimetallic Catalysts Supported on TiO2 for Selective CO2 Hydrogenation to Hydrocarbons," Journal of CO2 Utilization, May 1, 2018, 25:330-337, 8 pages.
Chen et al., "Trititanate Nanotubes Made vis a Single Alkali Treatment," Advanced Materials, Sep. 3, 2002, 17:1208-1211, 4 pages.
Kasuga et al., "Titania Nanotubes Prepared by Chemical Processing," Advanced Materials, Oct. 11, 1999, 15:1307-1311, 5 pages.
Ou et al., "Review of Titania Nanotubes Synthesized via the Hydrothermal Treatment: Fabrication, Modification, and Application," Separation Purification Technology, Dec. 1, 2007, 58:179-191, 13 pages.
Thalgaspitiya et al., "Generalized Synthesis of High Surface Area Mesoporous Metal Titanates as Efficient Heterogeneous Catalysts," Applied Materials Today, Jun. 1, 2020, 19:100570, 5 pages.
Wang et al., "Highly Selective Conversion of CO2 to Light Olefins via Fischer-Tropsch Synthesis Over Stable Layered K—Fe—Ti Catalysts," Applied Catalysis A: General, Mar. 5, 2019, 573:32-40, 9 pages.
Ji et al., "Application of titanate nanotubes for photocatalytic decontamination in water: challenges and prospects," ACS ES&T Engineering, Jan. 2022, 2(6):1015-1038, 2 pages (Abstract only).
Zafar et al., "Effect of different iron precursors on the synthesis and photocatalytic activity of Fe—TiO2 nanotubes under visible light," Ceramics International, Feb. 2020, 46(3):3353-3366, 54 pages.

* cited by examiner

*Primary Examiner* — Jafar F Parsa
(74) *Attorney, Agent, or Firm* — Fish & Richardson P.C.

(57) ABSTRACT

The disclosure relates to iron-doped potassium titanate nanotube catalysts, and methods of making and using such catalysts. The catalysts can be used in the hydrogenation of carbon dioxide ($CO_2$) for the production of light olefins.

20 Claims, 5 Drawing Sheets

IRON-DOPED POTASSIUM-TITANATE NANOTUBE CATALYSTS AND METHODS OF MAKING AND USING SAME

FIELD

The disclosure relates to iron-doped potassium titanate nanotube catalysts, and methods of making and using such catalysts. The catalysts can be used in the hydrogenation of carbon dioxide ($CO_2$) for the production of light olefins.

BACKGROUND

Carbon dioxide is a relatively abundant and non-toxic carbon source to provide value-added products (e.g., carbon monoxide, methanol, other single-carbon based hydrocarbons, hydrocarbons containing two or more carbons).

SUMMARY

The disclosure relates to iron-doped potassium titanate nanotube catalysts, and methods of making and using such catalysts. The catalysts can have a relatively high surface area. The catalysts can exhibit a mesoporous structure with a relatively narrow pore size distribution. Without wishing to be bound by theory, it is believed that the pore size of the catalysts and/or pore size distributions of the catalysts can allow for relatively high loading of iron with relatively high dispersion. Without wishing to be bound by theory, it is believed that the catalyst may include oxygen vacancies that can enhance the conversion of $CO_2$ by promoting $CO_2$ adsorption and activation.

The catalysts can be synthesized relatively easily, such as, for example, in a one-pot synthesis. The catalysts can be synthesized without the use of a structure-directing agent or template, which can be expensive, toxic and/or increase the complexity of the synthesis. Thus, the catalyst can be synthesized relatively easily, inexpensively and/or with a reduced environmental impact relatively to certain other methods of synthesizing catalysts. During synthesis of the catalysts, a solid solution (a solid composed of a relatively uniform and/or homogenous mixture of the constituents) can be formed over a relatively wide range of iron concentrations.

The catalysts can be used to convert carbon dioxide to value added products. As an example, the catalysts can be used in the hydrogenation of carbon dioxide to generate light olefin products, which have a relatively high energy density and value. In the hydrogenation of carbon dioxide, the catalyst can demonstrate a relatively high selectivity towards the formation of light olefins (e.g., ethylene, propylene, 1-butene). The light olefins generated using the catalysts and related methods of the disclosure can be used, for example, as a feedstock for producing plastics, fibers and other chemicals. The catalysts and methods of the disclosure can reduce carbon dioxide emissions related to the production of light olefins, relative to certain other methods of making light olefins. By consuming carbon dioxide, the catalysts can be employed as part of a carbon dioxide emission mitigation strategy.

In a first aspect, the disclosure provides a catalyst, including nanotubes including iron-doped potassium titanate.

In any or all embodiments, the nanotubes include multi-layered sidewalls defining pores having a size distribution of 3 nm to 6 nm.

In any or all embodiments, the catalyst includes from 5 weight percent (wt. %) to 25 wt. % iron.

In any or all embodiments, the catalyst includes from 5 weight percent (wt. %) to 25 wt. % potassium.

In any or all embodiments, for at least some of the nanotubes, the nanotubes include a titanate network, and at least some of the iron is in the titanate network.

In any or all embodiments, for at least some of the nanotubes, the nanotubes include multilayered sidewalls defining pores, and at least some of the iron is in the pores.

In any or all embodiments, the catalyst has a surface area of 144 square meters per gram ($m^2/g$) to 253 $m^2/g$.

In any or all embodiments, for at least some of the nanotubes, the nanotubes include a sidewall defining one or more pores, and the pores have a volume of 0.16 cubic centimeters per gram ($cm^3/g$) to 0.23 $cm^3/g$.

In any or all embodiments, the nanotubes include multi-layered sidewalls having an interlayer spacing between adjacent walls of 0.87 nanometers (nm) to 0.88 nm.

In a second aspect, the disclosure provides a method of hydrogenating carbon dioxide, using a catalyst of the present disclosure.

In any or all embodiments, the catalyst has a carbon dioxide conversion of at least 10%.

In any or all embodiments, the catalyst has an olefin selectivity of at least 5%.

In any or all embodiments, the catalyst has a paraffin selectivity of at most 25%.

In a third aspect, the disclosure provides a method, including forming a solution including an iron salt and a titanium source, and adding a mineralizing agent to the solution. The method forms a catalyst including iron-doped potassium titanate nanotubes.

In any or all embodiments, the method further includes, after adding the mineralization agent, heating the solution with agitation.

In any or all embodiments, heating the solution with agitation includes heating to a temperature of at 150° C. to 170° C. for 24 hours to 48 hours.

In any or all embodiments, the method further includes, after heating the solution with agitation: filtering the solution to obtain a first solid; washing the first solid with water to remove excess mineralization agent, thereby providing an intermediate; filtering the intermediate to obtain a second solid; redispersing the second solid to form a dispersion; adjusting a pH of the dispersion to a value of 7 to 8; and filtering the dispersion and drying to obtain the catalyst.

In any or all embodiments, the iron salt includes iron nitrate, iron sulfate, iron acetate, iron chloride and/or iron hydroxide.

In any or all embodiments, the titanium source includes amorphous titanium oxide, crystalline titanium oxide (e.g., anatase, rutile, and/or brookite), titanium chloride, titanium alkoxides (e.g., isopropoxide, butoxide, and/or ethoxide), titanium oxysulfate, titanium bis(ammonium lactate)dihydroxide, titanium (triethanolaminato) isopropoxide, titanium bis(acetylacetonate) diisopropoxide, chlorotriisopropoxide titanium, and/or potassium titanium oxide oxalate dihydrate.

In any or all embodiments, the mineralizing agent includes potassium hydroxide and/or sodium hydroxide.

In any or all embodiments, the iron salt includes iron nitrate, the titanium source includes potassium titanium oxide oxalate dihydrate, and the mineralization agent includes potassium hydroxide.

DETAILED DESCRIPTION

Catalysts

Figure 1:
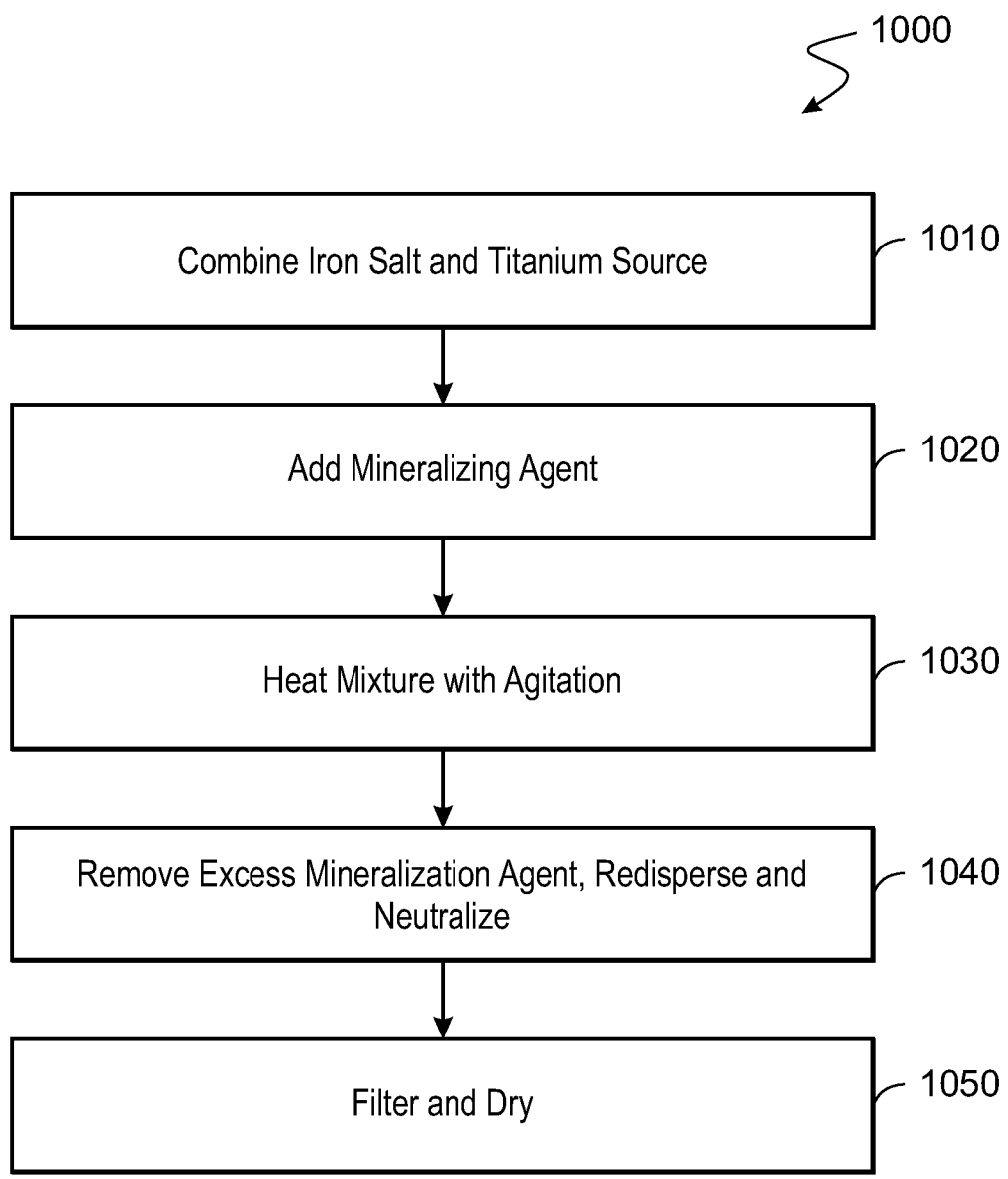
FIG. 1 depicts a flowchart of a method.

The iron-doped potassium titanate nanotubes comprise, consist essentially of or consist of iron-doped potassium titanate nanotube catalyst. The iron-doped potassium titanate nanotubes include sidewalls and pores defining a space within the sidewalls. The sidewalls are multilayered and include an interlayer spacing between these layers. Without wishing to be bound by theory, it is believed that the iron does not reside in the interlayer spacing of the iron-doped potassium titanate nanotubes. Rather it is believed that iron atoms may be present in the titanate network of the iron-doped potassium titanate nanotubes, and/or that iron atoms may occupy the pores of the iron-doped potassium titanate nanotubes.

In general, the amount of iron, potassium and titanate present in the iron-doped potassium titanate nanotube catalyst is selected to yield a desired structure (e.g., iron-doped potassium titanate nanotubes) and/or desired properties (e.g., performance as a carbon dioxide hydrogenation catalyst, relatively high selectivity for olefins in a carbon dioxide hydrogenation reaction, relatively high carbon dioxide conversion in a carbon dioxide hydrogenation reaction).

In any or all embodiments, the iron-doped potassium titanate nanotube catalyst includes at least 5 (e.g., at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24) wt. % iron and/or at most 25 (e.g., at most 24, at most 23, at most 22, at most 21, at most 20, at most 19, at most 18, at most 17, at most 16, at most 15, at most 14, at most 13, at most 12, at most 11, at most 10, at most 9, at most 8, at most 7, at most 6) wt. % iron. Without wishing to be bound by theory, it is believed that increasing the iron content increases the conversion of carbon dioxide and/or selectivity for light olefins.

Without wishing to be bound by theory, it is believed that the potassium serves as a counter ion to the titanate moiety. In certain embodiments, the iron-doped potassium titanate nanotube catalyst includes at least 5 (e.g., at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24) wt. % potassium and/or at most 25 (e.g., at most 24, at most 23, at most 22, at most 21, at most 20, at most 19, at most 18, at most 17, at most 16, at most 15, at most 14, at most 13, at most 12, at most 11, at most 10, at most 9, at most 8, at most 7, at most 6) wt. % potassium. Without wishing to be bound by theory, it is believed that the potassium enhances the selectivity for light olefins.

In any or all embodiments, the iron-doped potassium titanate nanotube catalyst includes at least 76 (e.g., at least 80) wt. % titanate and/or at most 85 (e.g., at most 80) wt. % titanate.

In general, the pores of the iron-doped potassium titanate nanotubes have a relatively narrow size distribution. In the same or other embodiments, the pore size distribution is at least 3 (e.g., at least 3.1, at least 3.2, at least 3.3, at least 3.4, at least 3.5, at least 3.6, at least 3.7, at least 3.8, at least 3.9, at least 4, at least 4.1, at least 4.2, at least 4.3, at least 4.4, at least 4.5, at least 4.6, at least 4.7, at least 4.8, at least 4.9, at most 5.0, at most 5.1, at most 5.2, at most 5.3, at most 5.4, at most 5.5, at most 5.6, at most 5.7, at most 5.8, at most 5.9) nm to at most 6 (e.g., at most 5.9, at most 5.8, at most 5.7, at most 5.6, at most 5.5, at most 5.4, at most, 5.3, at most 5.2, at most 5.1, at most 5.0, at most 4.9, at most 4.8, at most 4.7, at most 4.6, at most 4.5, at most 4.4, at most 4.3, at most 4.2, at most 4.1, at most 4, at most 3.9, at most 3.8, at most 3.7, at most 3.6, at most 3.5, at most 3.4, at most 3.3, at most 3.2, at most 3.1) nm. In some embodiments, the average pore size is at least 3.5 (e.g., at least 3.6, at least 3.7, at least 3.8) nm and/or at most 3.9 (e.g., at most 3.8, at most 3.7, at most 3.6) nm. Without wishing to be bound by theory, it is believed that size of any occluded materials in the pore will not exceed the size of the pore (e.g., 3.5 nm), which will reduce (e.g., prevent) excessive sintering of the active phase (iron).

Without wishing to be bound by theory, it is believed that the pore volume is sensitive to the iron content. In any or all embodiments, the average volume of the pores is at least 0.16 (e.g., at least 0.17, at least 0.18, at least 0.19, at least 0.2, at least 0.21, at least 0.22) cm$^3$/g and/or at most 0.23 (e.g., at most 0.22, at most 0.21, at most 0.2, at most 0.19, at most 0.18, at most 0.17) cm$^3$/g. Without wishing to be bound by theory, it is believed that the pore volume affects the amount of active phase (iron) occluded.

Without wishing to be bound by theory, it is believed that the surface area is sensitive to the iron content. In certain embodiments, the catalyst has a surface area (surface area of both inner and outer walls of the nanotubes) of at least 144 (e.g., at least 150, at least 160, at least 170, at least 180, at least 190, at least 200, at least 210, at least 220, at least 230, at least 240, at least 250) m$^2$/g and/or at most 253 (e.g., at most 250, at most 240, at most 230, at most 220, at most 210, at most 200, at most 190, at most 180, at most 170, at most 160, at most 150) m$^2$/g. Without wishing to be bound by theory, it is believed that a relatively large surface area is desirable.

In any or all embodiments, the walls of the iron-doped potassium titanate nanotubes have an interlayer spacing of 0.87 to 0.88 nm. Without wishing to be bound by theory, it is believed that the interlayer spacing can serve as a confirmation to the formation of nanotubes with multilayered sidewalls.

The iron-doped potassium titanate nanotubes include one or more X-ray diffraction (XRD) reflections that are characteristic of titanate nanotubes (see discussion below). In certain embodiments, 2-theta (±0.2 degrees) values for XRD reflections of the catalyst include at least one (e.g., at least two, at least three, at least four, at least 5) member(s) selected from the group consisting of 9.76°, 19.45°, 24.04°, 27.82°, 29.64°, 33.36°, 39.03°, 43.32°, 46.36°, 48.02°, 49.18°, 55.15°, 56.44°, 61.94°, 62.82°, 63.64° and 69.11° as measured as described below.

Methods of Making Catalysts

FIG. 1 depicts a flowchart for a method 1000 of making a catalyst. In step 1010, an iron salt and a titanium source are combined in water to form a mixture.

In general, the iron salt can be any water-soluble iron salt. Examples of the iron salt include iron nitrate, iron sulfate, iron acetate, iron chloride and iron hydroxide.

Generally, the amount of iron used in the step 1010 is selected so that the final product (iron-doped potassium titanate nanotube catalyst) has a desired structure (e.g., iron-doped potassium titanate nanotubes) and/or desired properties (e.g., performance as a carbon dioxide hydrogenation catalyst, relatively high selectivity for olefins in a carbon dioxide hydrogenation reaction, relatively high carbon dioxide conversion in a carbon dioxide hydrogenation reaction). In some embodiments, the amount of iron used in the step 1010 is at least 10 (e.g., at least 15, at least 20) wt. % and/or at most 25 (e.g., at most 20, at most 15) wt. %.

Examples of the titanium source include amorphous titanium oxide, crystalline titanium oxide (anatase, rutile, and/or brookite), titanium chloride, titanium alkoxides (isopropoxide, butoxide, and/or ethoxide), titanium oxysulfate, titanium bis(ammonium lactate)dihydroxide, titanium (triethanolaminato) isopropoxide, titanium bis(acetylacetonate) diisopropoxide, chlorotriisopropoxide titanium, and potassium titanium oxide oxalate dihydrate.

In step 1020, a mineralizing agent is added to the mixture. In general, the step 1020 can be performed under any appropriate conditions, which will be known to those ordinarily skilled in the art. In any or all embodiments, step 1020 includes homogenizing the mixture with stirring at a temperature of 15-30 (e.g., 15-20, 15-25, 20-25, 20-30, 25-30, 15, 20, 25, 30) ° C. for 1-2 (e.g., 1-1.25, 1-1.5, 1-1.75, 1.25-1.5, 1.25-1.75, 1.25-2, 1.5-1.75, 1.5-2, 1.75-2, 1, 1.25, 1.5, 1.75, 2) hours.

Examples of the mineralizing agent include solid potassium hydroxide, solid sodium hydroxide, liquid potassium hydroxide or sodium hydroxide aqueous solution. Without wishing to be bound by theory, it is believed that the mineralizing agent generates the iron-doped potassium titanate nanotubes of the catalyst. Nanotubes are generated rather than nanorods.

Without wishing to be bound by theory, it is believed that potassium in the catalyst is from both potassium in the titanate source and mineralization agent.

In general, the amount of the mineralizing agent is selected so that the final product (iron-doped potassium titanate nanotube catalyst) has a desired structure and/or properties. In general, an excess of mineralization agent is added in the step 1020. In any or all embodiments, the concentration of the mineralization agent (e.g., KOH) in the step 1020 is at least 6 (e.g., at least 7, at least 8) M and/or at most 9 (e.g., at most 8, at most 7) M. In any or all embodiments, the concentration of the mineralization agent (e.g., KOH) in the step 1020 is 7 M.

In step 1030, the mixture is heated with agitation to form a solid in the mixture. The heating can be performed, for example, in an autoclave with mixing performed by mechanically tumbling the autoclave. In general, heating and mixing can be performed under any appropriate conditions. In any or all embodiments, the mixture is heated at 150-170 (e.g., 150-155, 150-160, 150-165, 155-160, 155-165, 155-170, 160-165, 160-170, 165-170, 150, 155, 160, 165, 170) ° C. for a time period of 24-48 (e.g., 24-36, 36-24, 24, 36, 48) hours.

Generally, the steps 1010, 1020 and 1030 can be performed using any appropriate equipment, which is commercially available and known to those ordinarily skilled in the art. In any or all embodiments, the steps 1010, 1020 and 1030 can be performed as a one pot hydrothermal synthesis without the use of a template.

In the step 1040, the solid product is filtered from the other constituents in the mixture to obtain a first solid. The first solid is washed with water to remove excess mineralizing agent. A second solid is obtained by filtering and the second solid is re-dispersed in water to form a dispersion. The dispersion is neutralized to a pH of 7-8. Neutralization can be performed using a dilute acidic solution, e.g., a dilute solution of nitric acid, a dilute solution of sulfuric acid, a dilute solution of acetic acid or a dilute solution of hydrochloric acid.

In the step 1050, the dispersion is filtered and dried to provide the catalyst. In general, any appropriate method of filtering can be used in the steps 1040 and 1050. The filtering can be performed, for example, using a funnel and filter paper. Generally, the drying that occurs in the step 1050 can be performed at any appropriate temperature. In any or all embodiments, drying the solids in step 1050 is performed at a temperature of 85-120 (e.g., 85-90, 85-95, 85-100, 85-105, 85-110, 85-115, 90-95, 90-100, 90-105, 90-110, 90-115, 90-120, 95-100, 95-105, 95-110, 95-115, 95-120, 100-105, 100-110, 100-115, 100-120, 105-110, 105-115, 105-120, 110-115, 110-120, 115-120, 85, 90, 95, 100, 105, 110, 115, 120) ° C. for at least 24 (e.g., at least 30, at least 36, at least 42, at least 48) hours.

Methods of Using Catalysts for Carbon Dioxide Hydrogenation

The catalysts can be used in the hydrogenation of carbon dioxide and can demonstrate relatively high selectivity for light olefins (e.g., ethylene, propylene, 1-butene).

Prior to use, the catalyst are reductively activated. The catalysts can be reductively activated by heating in the presence of a reducing gas such as hydrogen. In some embodiments, the reductive activation is performed at a temperature of 550° C.

Carbon dioxide hydrogenation can be performed in the presence of carbon dioxide and hydrogen gas. In any or all embodiments, the hydrogen gas is present in an excess. In some embodiments, the ratio of hydrogen gas to carbon dioxide is at least 1:1 (e.g., at least 2:1, at least 3:1, at least 4:1, at least 5:1) and/or at most 6:1 (e.g., at most 5:1, at most 4:1, at most 3:1, at most 2:1). In any or all embodiments, the reaction temperature is at least 250 (e.g., at least 300, at least 350) ° C. and/or at most 400 (e.g., at most 350, at most 300) ° C. In the same or other embodiments, the reaction pressure is at least 0.01 (e.g., at least 0.02, at least 0.05, at least 0.1, at least 0.2 at least 0.5, at least 1, at least 2, at least 5, at least 10, at least 15, at least 20, at least 25) barg and/or at most 30 (e.g., at most 25, at most 20, at most 15, at most 10, at most 5, at most 2, at most 1, at most 0.5, at most 0.2, at most 0.1, at most 0.05, at most 0.02) barg. Without wishing to be bound by theory, it is believed that the reaction conditions (e.g., the ratio of hydrogen gas to carbon dioxide, the reaction temperature, the reaction pressure) can be selected to maximize activity, selectivity and/or stability.

In addition to olefins (e.g., ethylene, propylene, 1-butene), the reaction can generate paraffins (e.g., methane, ethane, propane, n-butane) and/or alcohols (e.g., methanol, ethanol, propanol, butanol). Unconverted hydrogen and/or carbon dioxide can be recovered from the product stream and recycled for subsequent reactions.

As used herein, the carbon dioxide conversion is calculated as $$X_{CO_2} = \frac{\left(F_{in} \times y_{in}^{CO_2} - F_{out} \times y_{out}^{CO_2}\right)}{F_{in} \times y_{in}^{CO_2}} \times 100\%$$

as measured at 48 hours of the catalyst on the stream composed of $H_2$ and $CO_2$ at a ratio of 3:1, at a temperature of 325° C., a pressure of 20 barg, and a gas hourly space velocity (GHSV) of 6600 milliliters (gram cat.)$^{-1}$hour$^{-1}$. $F_{in}$ and $F_{out}$ represented the molar flow of inlet and outlet gas respectively. $y_{in}$ and $y_{out}$ are $CO_2$ fraction in the infeed and tail gas. $X_{CO2}$ represented the conversion of $CO_2$. In any or all embodiments, the catalyst has a carbon dioxide conversion of at least 5 (e.g., at least 10, at least 15, at least 20, at least 25) %.

As used herein, an olefin or paraffin selectivity is calculated as $$S_i = \frac{F_{out} \times y_{out}^i}{\left(F_{in} \times y_{in}^{CO_2} \times X_{CO_2}\right)} \times 100\%$$

as measured at 48 hours of the catalyst on stream composed of $H_2$ and $CO_2$ at a ratio of 3:1, at a temperature of 325° C., a pressure of 20 barg, and a gas hourly space velocity (GHSV) of 6600 milliliters (gram cat.)$^{-1}$ hour$^{-1}$. The selectivity of a given hydrocarbon is $S_i$ wherein i represents each hydrocarbon. In any or all embodiments, the catalyst has an olefin selectivity of at least 5 (e.g., at least 10, at least 15, at least 20, at least 25, at least 20, at least 35, at least 40, at least 45, at least 50, at least 55) %. In any or all embodiments, the catalyst has a paraffin selectivity of at least 1 (e.g., at least 2, at least 5, at least 10, at least 15, at least 20, at least 25) % and/or at most 30 (e.g., at most 25, at most 20, at most 15, at most 10, at most 5) %.

EXAMPLES

Example 1: Synthesis of Fe-K-TiNT-1 (10 wt. % Iron)

1.804 g iron nitrate (Fe(NO$_3$)$_3$·9H$_2$O) was dissolved in 14.52 g of deionized water. 9.954 g of potassium titanium oxide oxalate dihydrate (C$_4$K$_2$O$_9$Ti·2H$_2$O) was added to the iron solution under stirring. The dispersion was stirred at room temperature for 30 minutes. To set the potassium hydroxide (KOH) concentration in the final mixture to 7 M, 18.48 ml of 12.5 M KOH solution was added dropwise to the stirring dispersion. The mixture was homogenized by further stirring at room temperature for 2 hours. The mixture was transferred to a Teflon-lined stainless-steel autoclave and heated at 165° C. for 24 hours with agitation by mechanically tumbling the autoclave.

After heating, the autoclave was cooled to ambient temperature and the contents were filtered, washed with 100 ml deionized water three times, filtered, and re-dispersed in 100 ml deionized water. The pH of the product dispersion was lowered to 8 by the dropwise addition of 0.2 M nitric acid (HNO$_3$) solution. The solid product was then filtered and dried at 100° C. to yield the catalyst (Fe-K-TiNT-1).

Example 2: Synthesis of Fe-K-TiNT-2 (15 wt. % Iron)

2.866 g iron nitrate (Fe(NO$_3$)$_3$·9H$_2$O) was dissolved in 14.52 g of deionized water. 9.954 g potassium titanium oxide oxalate dihydrate (C$_4$K$_2$O$_9$Ti·2H$_2$O) was added to the iron solution under stirring. The dispersion was stirred at room temperature for 30 minutes. To set the potassium hydroxide (KOH) concentration in the final mixture to 7 M, 18.48 ml of 12.5 M KOH solution was added dropwise to the stirring dispersion. The mixture was homogenized by further stirring at room temperature for 2 hours. The mixture was transferred to a Teflon-lined stainless-steel autoclave and heated at 165° C. for 24 hours with agitation by mechanically tumbling the autoclave.

After heating, the autoclave was cooled to ambient temperature and the contents were filtered, washed with 100 ml deionized water three times, filtered, and re-dispersed in 100 ml deionized water. The pH of the product dispersion was lowered to 8 by the dropwise addition of 0.2 M nitric acid (HNO$_3$) solution. The solid product was then filtered and dried at 100° C. to yield the catalyst (Fe-K-TiNT-2).

Example 3: Synthesis of Fe-K-TiNT-3 (20 wt. % Iron)

4.060 g iron nitrate (Fe(NO$_3$)$_3$·9H$_2$O) was dissolved in 14.52 g of deionized water. 9.954 g potassium titanium oxide oxalate dihydrate (C$_4$K$_2$O$_9$Ti·2H$_2$O) was added to the iron solution under stirring. The dispersion was stirred at room temperature for 30 minutes. To set the potassium hydroxide (KOH) concentration in the final mixture to 7 M, 18.48 ml of 12.5 M KOH solution was added dropwise to the stirring dispersion. The mixture was homogenized by further stirring at room temperature for 2 hours. The mixture was transferred to a Teflon-lined stainless-steel autoclave and heated at 165° C. for 24 hours with agitation by mechanically tumbling the autoclave.

After heating, the autoclave was cooled to ambient temperature and the contents were filtered, washed with 100 ml deionized water three times, filtered, and re-dispersed in 100 ml deionized water. The pH of the product dispersion was lowered to 8 by the dropwise addition of 0.2 M nitric acid (HNO$_3$) solution. The solid product was then filtered and dried at 100° C. to yield the catalyst (Fe-K-TiNT-3).

Example 4: Synthesis of Fe-K-TiNT-4 (25 wt. % Iron)

5.413 g iron nitrate (Fe(NO$_3$)$_3$·9H$_2$O) was dissolved in 14.52 g of deionized water. 9.954 g potassium titanium oxide oxalate dihydrate (C$_4$K$_2$O$_9$Ti·2H$_2$O) was added to the iron solution under stirring. The dispersion was stirred at room temperature for 30 minutes. To set the potassium hydroxide (KOH) concentration in the final mixture to 7 M, 18.48 ml of 12.5 M KOH solution was added dropwise to the stirring dispersion. The mixture was homogenized by further stirring at room temperature for 2 hours. The mixture was transferred to a Teflon-lined stainless-steel autoclave and heated at 165° C. for 24 hours with agitation by mechanically tumbling the autoclave.

After heating, the autoclave was cooled to ambient temperature and the contents were filtered, washed with 100 ml deionized water three times, filtered, and re-dispersed in 100 ml deionized water. The pH of the product dispersion was lowered to 8 by the dropwise addition of 0.2 M nitric acid (HNO$_3$) solution. The solid product was then filtered and dried at 100° C. to yield the catalyst (Fe-K-TiNT-4).

Example 5: X-Ray Diffraction Analysis

XRD patterns of the catalysts were obtained using a Rigaku MiniFlex-600 X-ray Diffractometer with Cu Kα (λ=0.154059 nm) radiation, fixed slit incidence (0.25° divergence, 0.5° anti-scatter, specimen length of 10 mm) and diffracted optics (0.25° anti-scatter, 0.02 mm nickel filter). Data was obtained at 40 kV and 15 mA from 5 to 75 (2θ) using a PIXcel detector with a PSD length of 3.350 (2θ), and 255 active channels.

Figure 2:
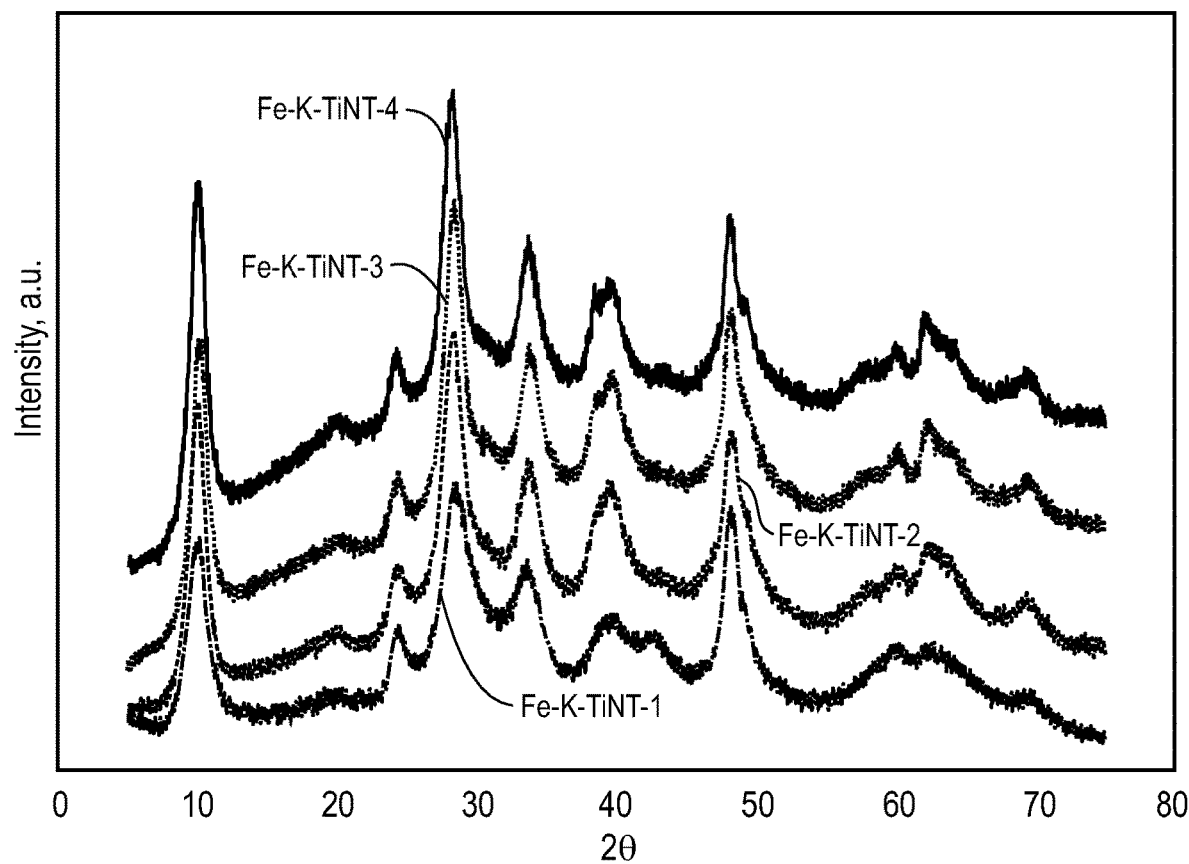
FIG. 2 shows X-ray diffraction (XRD) data.

The formation of iron-doped potassium titanate nanotubes was characterized by the emergence of a broad low angle reflection between 7.2° and 10.3° 2θ in the XRD pattern, as shown in FIG. 2, corresponding to reflection from the (200) plane and was characteristic of titanate nanotubes. This peak was attributed to the interlayer spacing (d-spacing) of the layered titanate phase, as shown in Table 1, and was calculated using the Bragg's equation. The interlayer spacing values for all samples were nearly identical, regardless of iron loading. Thus, the iron does not reside in the interlayer spacing of the nanotubes. The major diffraction reflections at about 2θ=9.76°, 19.45°, 24.04°, 27.82°, 29.64°, 33.36°, 39.03°, 43.32°, 46.36°, 48.02°, 49.18°, 55.15°, 56.44°, 61.94°, 62.82°, 63.64° and 69.11° were observed for all the samples, which correspond to the (200), (400), (110), (310), (600), (301), (501), (411), (701), (020), (220), (901), (811), (002), (202), (521) and (721) planes of $H_2Ti_2O_5 \cdot H_2O/K_xH_{2-x}Ti_2O_5 \cdot H_2O$ (JCPDS No. 47-0124). Therefore, the iron may be present in the titanate network and/or occupying space within the tubes as with increasing iron content, there was no increase in the interlayer spacing and no distinct XRD iron reflection was detected.

Example 6: Nitrogen Sorption Analysis

The catalyst surface area, pore volume and average pore diameter were determined from $N_2$ sorption isotherms at 77 K using fully automated Quadrasorb-evo (Quantachrome) surface area and porosity analyzer. Before analysis, all samples (0.20-0.25 g) were degassed under $N_2$ at 363 K for 1 h and 473 K for 12 h. From the isotherms, the Brunauer-Emmett-Teller (BET) method was used to determine the surface area, while the Barrett-Joyner-Halenda (BJH) model was used for calculation of pore volume and average pore diameter of the catalysts.

Figure 3:
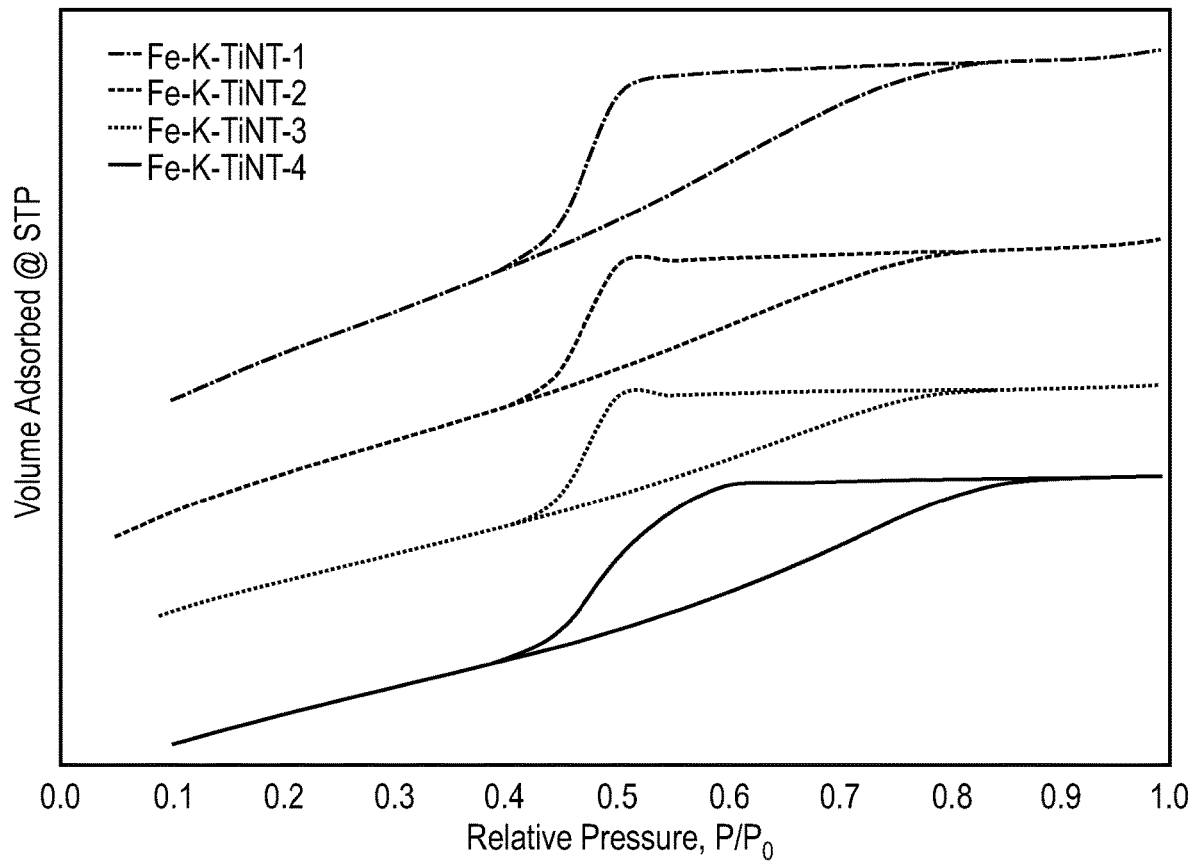
FIG. 3 shows nitrogen-sorption isotherm data.

FIG. 3 shows the nitrogen-sorption isotherms for each of the catalysts. Nitrogen-sorption measurements displayed similar isotherm shape for all the catalysts, and were classified as type-IV isotherm with type-$H_2$ hysteresis, as shown in FIG. 3, corresponding to multilayer adsorption on surface of mesoporous materials.

Figure 4:
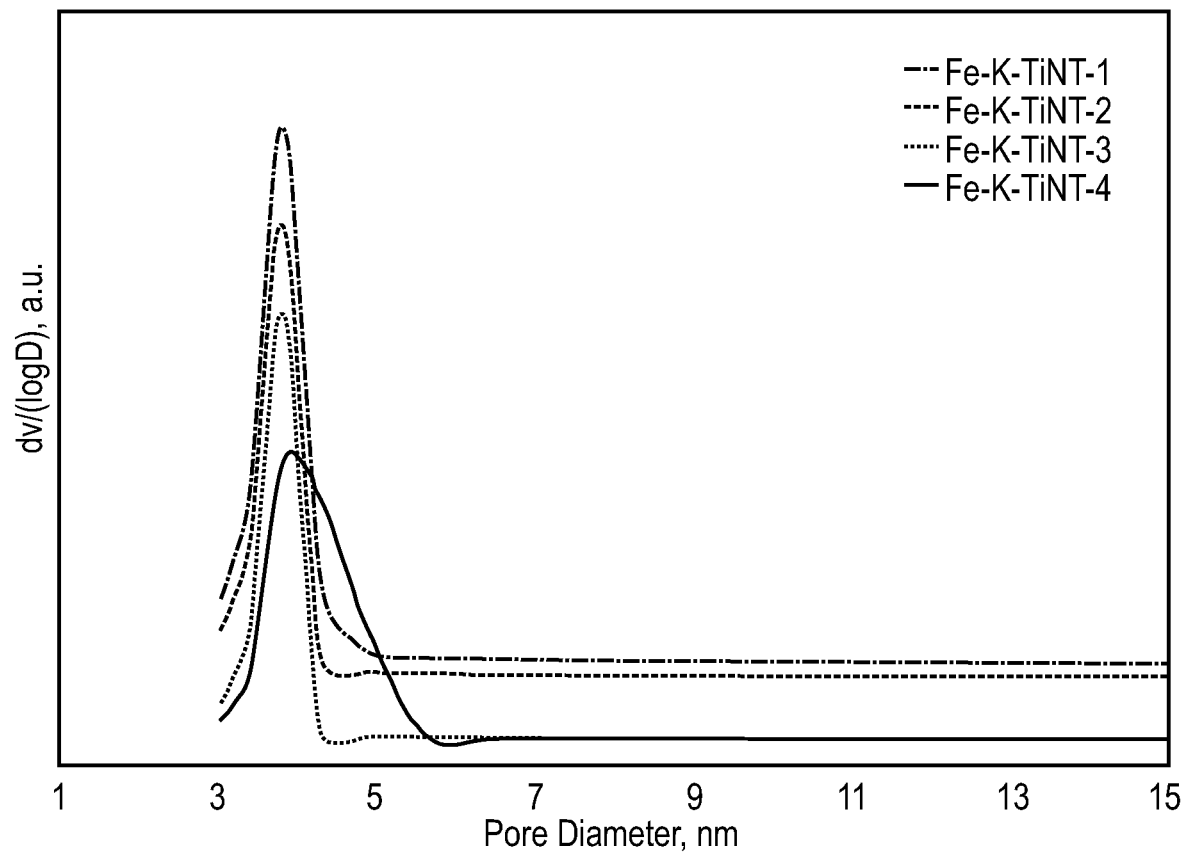
FIG. 4 shows BJH pore-size distribution profiles.

FIG. 4 shows the BJH pore-size distribution analysis. BJH pore-size distribution curves for catalysts with iron loading less than 25 wt. % exhibited a monomodal and relatively narrow pore-size distribution ranging from 3-4.8 nm and centered at about 3.8 nm, as shown in FIG. 4. The catalyst with the iron loading of ~25 wt. % (Fe-K-TiNT-4) had a relatively broader pore-size distribution ranging from 3-6 nm, suggesting the possible formation of deformed mesopores potentially caused by a non-uniform distribution of iron in the titanate matrix.

The values of the mesopore diameter were the same (~3.84 nm) for all samples, as shown in Table 1, while the BET surface area and pore volume of the samples were found to decrease with increasing iron content in the iron-doped potassium titanate nanotubes. These results suggest the formation of a solid solution through the insertion of iron ions into the titanate network, which increased the grain-size (fine crystals that make up the sheets of the walls of the nanotubes) of the nanotubes with increasing iron content. The enlargement of the grain-size decreased the surface area and pore volume of the crystalline materials.

TABLE 1

Physiochemical properties of the catalysts

|  | Fe-K-TiNT-1 | Fe-K-TiNT-2 | Fe-K-TiNT-3 | Fe-K-TiNT-4 |
|---|---|---|---|---|
| *Fe content, wt. % | 6.86 | 9.91 | 13.63 | 14.42 |
| *K content, wt. % | 8.86 | 10.33 | 9.44 | 8.95 |

TABLE 1-continued

Physiochemical properties of the catalysts

|  | Fe-K-TiNT-1 | Fe-K-TiNT-2 | Fe-K-TiNT-3 | Fe-K-TiNT-4 |
|---|---|---|---|---|
| [1]Surface area, $m^2/g$ | 253 | 208 | 176 | 144 |
| [2]Pore volume, $cm^3/g$ | 0.232 | 0.185 | 0.161 | 0.156 |
| [3]Pore diameter, nm | 3.84 | 3.84 | 3.83 | 3.84 |
| [4]Interlayer spacing, nm | 0.88 | 0.89 | 0.87 | 0.88 |

*As measured by (Inductive Coupled Plasma-Atomic Spectroscopy) ICP-AS. The balance of the weight from ICP-AS is expected to be titanium dioxide
[1]Determined by BET analysis using nitrogen-sorption measurements
[2]Total pore volume for pores with Diameter less than 216.96 nm at P/Po = 0.991064.
[3]Calculated by the BJH method using desorption isotherm
[4]Calculated using the low angle XRD reflection ascribed to the interlayer spacing of the layered wall of the iron-doped potassium titanate nanotubes.

Example 7: Catalyst Preparation, Activation and Testing

Figure 5:
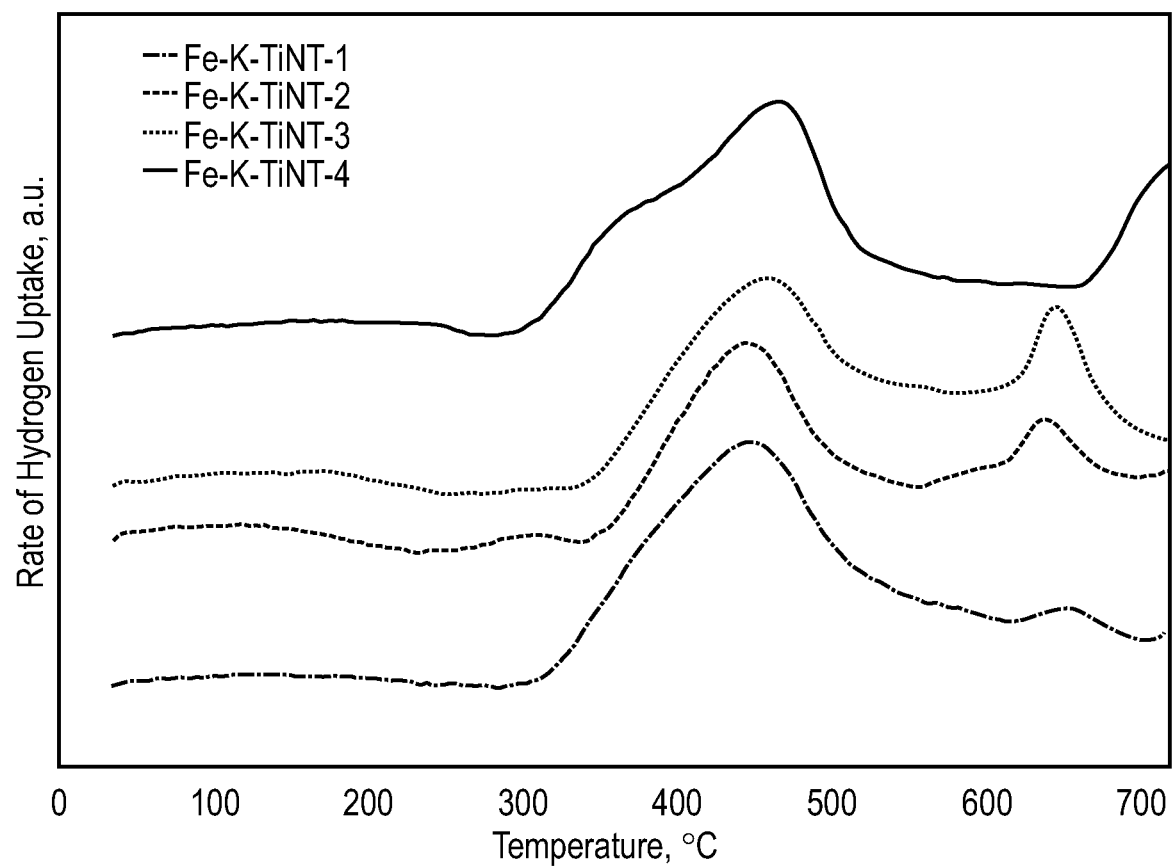
FIG. 5 show Hydrogen-Temperature Programmed Reduction ($H_2$-TPR) profiles.

In order to determine the proper activation protocol for the catalysts, Hydrogen-Temperature Programmed Reduction ($H_2$-TPR) analysis was conducted on the samples. The $H_2$-TPR profile of the samples indicates that the complete reduction of $Fe^{3+}$ to $Fe^{2+}$ or $Fe^+$ occurred at 550° C., as shown in FIG. 5. This relatively high reduction temperature is due the strong interaction between the iron and the titanate network resulting from their formation of a solid solution.

The catalysts as prepared in Examples 1-4 were pressed at 8 tones pressure to form tablets and crushed and sieved to form 200 to 500 micrometer granules. The granules (approx. 1.5 $cm^3$, 0.50 grams) were packed into a tubular Hastelloy-X reactor that was 310 mm in length and 9.1 mm internal diameter. The reactor had a thermocouple immersed in the catalyst bed.

To activate the catalysts, hydrogen (approx. 75 $cm^3$/min) was passed over the catalyst and the reactor's temperature was raised to 550° C. at the rate of 5° C./min and kept at 550° C. for at least 4 hours. The temperature was then lowered to the reaction temperature at a rate of 5° C./min.

The activated catalysts as described above were tested for the hydrogenation of $CO_2$ in a continuous flow reactor. The reactions were run at 325° C., 20 barg pressure, a $H_2$ to $CO_2$ ratio of 3:1 and a GHSV of 6600 milliliters (gram cat.)$^{-1}$ hour$^{-1}$.

Table 2 lists the reaction results obtained after 48 hours on stream by online gas chromatography. Conversion of $CO_2$ was found to increase with iron content in the catalyst, reaching a maximum of ~22% for the Fe-K-TiNT-4 catalyst. Likewise, olefin (ethylene, propylene, 1-butene and traces of 1-pentene) selectivity increased with iron loading, reaching a maximum of 45% over the Fe-K-TiNT-4 catalyst, but the highest olefin to paraffin (methane, ethane, propane, n-butane) ratio of 2.6 was obtained for the 7Fe-K-TiNT-3 catalyst. The balance of the product selectivity was due to CO and trace amounts of light alcohols (methanol, ethanol, propanol, butanol).

TABLE 2

Catalyst Performance in $CO_2$ hydrogenation reaction after 48 hours on stream.

| Catalyst | $CO_2$ Conversion, % | Olefin Selectivity, %[a] | Paraffin Selectivity, %[b] |
|---|---|---|---|
| Fe-K-TiNT-1 | 14.2 | 9.7 | 7.5 |
| Fe-K-TiNT-2 | 16.8 | 20.2 | 14.4 |

TABLE 2-continued

Catalyst Performance in $CO_2$ hydrogenation reaction after 48 hours on stream.

| Catalyst | $CO_2$ Conversion, % | Olefin Selectivity, %[a] | Paraffin Selectivity, %[b] |
|---|---|---|---|
| Fe-K-TiNT-3 | 18.1 | 39.9 | 15.4 |
| Fe-K-TiNT-4 | 22.2 | 45.2 | 20.9 |

[a]Olefins were ethylene, propylene, 1-butene
[b]Paraffins included methane, ethane, propane, n-butane

What is claimed:

1. A catalyst, comprising:
   iron-doped potassium titanate nanotubes;
   wherein the catalyst has a surface area of 144 square meters per gram ($m^2$/g) to 253 $m^2$/g; and
   wherein, for at least some of the nanotubes, the nanotube comprises a sidewall defining one or more pores, and the pores have a volume of 0.16 cubic centimeters per gram ($cm^3$/g) to 0.23 $cm^3$/g.

2. The catalyst of claim 1, wherein the nanotubes comprise multilayered sidewalls defining pores having a size distribution of 3 nm to 6 nm.

3. The catalyst of claim 1, wherein the catalyst comprises from 5 weight percent (wt. %) to 25 wt. % iron.

4. The catalyst of claim 1, wherein the catalyst comprises from 5 weight percent (wt. %) to 25 wt. % potassium.

5. The catalyst of claim 1, wherein at least one of the following characteristics holds for at least some of the nanotubes:
   the nanotubes comprise a titanate network, and at least some of the iron is in the titanate network; or
   the nanotubes comprise multilayered sidewalls defining pores, and at least some of the iron is in the pores.

6. The catalyst of claim 1, wherein the nanotubes comprise multi-layered sidewalls having an interlayer spacing between adjacent walls of 0.87 nanometers (nm) to 0.88 nm.

7. A method of hydrogenating carbon dioxide, comprising using the catalyst as defined by claim 1.

8. The method of claim 7, wherein the catalyst has a carbon dioxide conversion of at least 10%.

9. The method of claim 7, wherein the catalyst has an olefin selectivity of at least 5%.

10. The method of claim 7, wherein the catalyst has a paraffin selectivity of at most 25%.

11. The catalyst of claim 1, wherein for at least some of the nanotubes, the nanotubes comprise a titanate network, and at least some of the iron is in the titanate network.

12. The catalyst of claim 1, wherein for at least some of the nanotubes, the nanotubes comprise multilayered sidewalls defining pores, and at least some of the iron is in the pores.

13. The catalyst of claim 1, wherein the nanotubes comprise one or more X-ray diffraction (XRD) reflections that are characteristic of titanate nanotubes.

14. The catalyst of claim 13, wherein 2-theta (±0.2 degrees) values for XRD reflections of the catalyst comprise at least one member selected from the group consisting of 9.76°, 19.45°, 24.04°, 27.82°, 29.64°, 33.36°, 39.03°, 43.32°, 46.36°, 48.02°, 49.18°, 55.15°, 56.44°, 61.94°, 62.82°, 63.64° and 69.11°.

15. The catalyst of claim 13, wherein 2-theta (±0.2 degrees) values for XRD reflections of the catalyst comprise at least two members selected from the group consisting of 9.76°, 19.45°, 24.04°, 27.82°, 29.64°, 33.36°, 39.03°, 43.32°, 46.36°, 48.02°, 49.18°, 55.15°, 56.44°, 61.94°, 62.82°, 63.64° and 69.11°.

16. The catalyst of claim 13, wherein 2-theta (±0.2 degrees) values for XRD reflections of the catalyst comprise at least three members selected from the group consisting of 9.76°, 19.45°, 24.04°, 27.82°, 29.64°, 33.36°, 39.03°, 43.32°, 46.36°, 48.02°, 49.18°, 55.15°, 56.44°, 61.94°, 62.82°, 63.64° and 69.11°.

17. The catalyst of claim 1, wherein the catalyst consists essentially of the iron-doped potassium titanate nanotubes.

18. The catalyst of claim 1, wherein the catalyst consists of the iron-doped potassium titanate nanotubes.

19. The catalyst of claim 1, wherein the catalyst comprises a broad low angle reflection between 7.2° and 10.3° 2θ in an XRD pattern.

20. The catalyst of claim 1, wherein the nanotubes comprise multilayered sidewalls defining pores having a size distribution of 3 nm to 4.8 nm.

* * * * *

UNITED STATES PATENT AND TRADEMARK OFFICE
CERTIFICATE OF CORRECTION

PATENT NO. : 12,383,889 B2  
APPLICATION NO. : 18/106182  
DATED : August 12, 2025  
INVENTOR(S) : Mohammed Abdulmajeed Al-Daous Page 1 of 1

It is certified that error appears in the above-identified patent and that said Letters Patent is hereby corrected as shown below:

On the Title Page

Column 2, Line 1, under item (56), Other Publications delete "physis" insert -- physics --.

In the Claims

Column 12, Line 14, Claim 14, delete "(+0.2" insert -- (±0.2 --.

Signed and Sealed this  
Seventh Day of October, 2025

John A. Squires  
*Director of the United States Patent and Trademark Office*